(12) United States Patent
Noda et al.

(10) Patent No.: US 12,343,272 B2
(45) Date of Patent: Jul. 1, 2025

(54) STENT DELIVERY DEVICE

(71) Applicant: OLYMPUS CORPORATION, Hachioji (JP)

(72) Inventors: Kazuhiro Noda, Hadano (JP); Yuko Kirino, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 1073 days.

(21) Appl. No.: 17/329,898

(22) Filed: May 25, 2021

(65) Prior Publication Data

US 2021/0275338 A1 Sep. 9, 2021

Related U.S. Application Data

(63) Continuation of application No. PCT/JP2018/043625, filed on Nov. 27, 2018.

(51) Int. Cl.
*A61F 2/966* (2013.01)
*A61F 2/95* (2013.01)
*A61F 2/962* (2013.01)

(52) U.S. Cl.
CPC ....... *A61F 2/966* (2013.01); *A61F 2002/9511* (2013.01); *A61F 2002/9623* (2020.05)

(58) Field of Classification Search
CPC .............. A61F 2/966; A61F 2002/9511; A61F 2002/9623; A61F 2/04; A61F 2/82; A61F 2/848; A61F 2002/041; A61F 2002/8483
See application file for complete search history.

(56) References Cited

U.S. PATENT DOCUMENTS

2005/0085891 A1* 4/2005 Goto .................. A61F 2/95
623/1.11
2009/0312829 A1* 12/2009 Aoba .................. A61F 2/95
623/1.11

(Continued)

FOREIGN PATENT DOCUMENTS

CN 106102663 A 11/2016
CN 106999239 A 8/2017

(Continued)

OTHER PUBLICATIONS

Mar. 5, 2019 Search Report issued International Patent Application No. PCT/JP2018/043625.

(Continued)

*Primary Examiner* — Jerrah Edwards
*Assistant Examiner* — Jose H. Trevino, III
(74) *Attorney, Agent, or Firm* — Oliff PLC

(57) ABSTRACT

A stent delivery device that can be inserted into an endoscope. The device includes a guide catheter including a guide tube, an operating wire, and a joint portion that joins the guide tube and the wire. The device also includes a pusher catheter including a first tube through which the wire is inserted and a second tube through which the guide tube is inserted. The device may include a bite prevention portion that can prevent the wire from biting into an inner surface of the second tube. In a state where a distal end of the pusher catheter protrudes from the endoscope channel and the channel includes a curved portion in a curved state, a proximal end of the guide tube, which includes the joint portion, and/or the bite prevention portion can be positioned proximal of a proximal end of the curved portion in the endoscope channel.

20 Claims, 8 Drawing Sheets

(56) References Cited

U.S. PATENT DOCUMENTS

| | | | |
|---|---|---|---|
| 2012/0302952 A1* | 11/2012 | Kitada | A61M 25/0043 |
| | | | 604/525 |
| 2016/0074149 A1* | 3/2016 | Tanaka | A61F 2/915 |
| | | | 427/2.25 |
| 2017/0000318 A1* | 1/2017 | Miyano | A61F 2/94 |

FOREIGN PATENT DOCUMENTS

| | | |
|---|---|---|
| JP | 2009-297502 A | 12/2009 |
| WO | 2015/146321 A1 | 10/2015 |
| WO | 2017/213139 A1 | 12/2017 |
| WO | 2018/151051 A1 | 8/2018 |

OTHER PUBLICATIONS

Sep. 19, 2023 Office Action issued in Chinese Patent Application No. 201880099736.5.

\* cited by examiner

STENT DELIVERY DEVICE

CROSS REFERENCE TO RELATED APPLICATIONS

This application is a continuation application based on a PCT Patent Application No. PCT/JP2018/043625, filed on Nov. 27, 2018, the entire content of which is hereby incorporated by reference.

TECHNICAL FIELD

The present disclosure relates to a stent delivery device.

BACKGROUND

As a treatment for bile duct stenosis, a stent is known to be placed in the bile duct. It may be necessary to replace the stent due to blockage of the indwelling stent.

A known stent delivery device includes a stent, a guide catheter, and a pusher catheter. The stent is introduced into the body with the distal end of the guide catheter inserted. After moving the stent to the desired position, the distal end of the guide catheter inserted through the stent is retracted and pulled out from the stent to release the stent.

SUMMARY

There are two types of stent delivery devices, over-the-wire type and monorail type. In the monorail type, the guide wire inserted into the distal end of the guide catheter is pulled out from the hole formed on the side surface of the pusher catheter. The monorail type can perform the procedure with a shorter guide wire than the over-the-wire type.

Although the details will be described later, in the monorail type stent delivery device, the force required for the retracting operation of the guide catheter when releasing the stent becomes large, and the operation may become complicated.

Based on the above circumstances, it is an object of the present disclosure to provide a stent delivery device that suppresses an increase in the force required for retracting a guide catheter while maintaining a monorail type structure.

The present disclosure is directed to a stent delivery device that can be inserted into a channel of an endoscope that includes a portion capable of being curved. The stent delivery device includes: a guide catheter including a guide tube, an operating wire, and a joint portion that joins the guide tube and a distal end of the wire; and a pusher catheter including a first tube through which the operating wire has been inserted and a second tube through which the guide tube has been inserted. The stent delivery device may include a bite prevention portion that is designed to prevent the operating wire from biting into an inner surface of the second tube.

In a state where a distal end of the pusher catheter protrudes from the channel of the endoscope and the channel of the endoscope includes a curved portion that is in a curved state, a proximal end of the guide tube, which includes the joint portion, can be positioned proximal to a proximal end of the curved portion in the endoscope channel. Alternatively, or additionally, in the state where the distal end of the pusher catheter protrudes from the channel of the endoscope and the channel of the endoscope includes the curved portion, the bite prevention portion can be positioned proximal of a proximal end of the curved portion in the endoscope channel.

According to the present disclosure, it is possible to provide a stent delivery device that suppresses an increase in the force required for a retracting operation of a guide catheter while maintaining a monorail type structure.

DETAILED DESCRIPTION OF EMBODIMENTS

An exemplary embodiment of the present disclosure will be described with reference to FIGS. 1 to 7.

Figure 1:
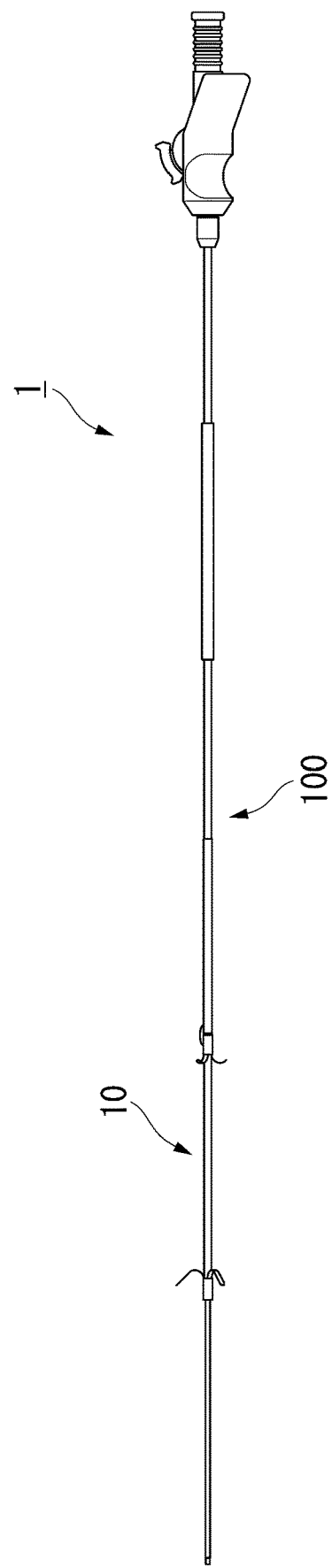
FIG. 1 is an overall view of a stent delivery device according to an embodiment of the present disclosure.

FIG. 1 is an overall view of a stent delivery device 1 of the present embodiment. The stent delivery device includes a stent 10 and a delivery catheter 100.

Figure 2:
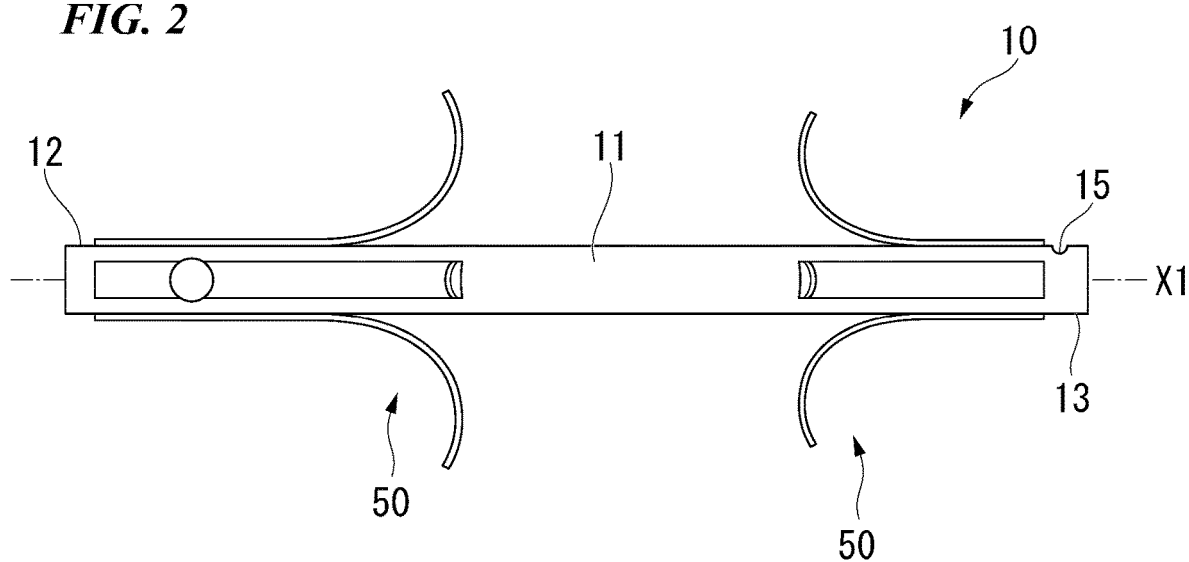
FIG. 2 is a side view of a stent according to the stent delivery device.

FIG. 2 is a side view of the stent 10. The stent 10 of the present embodiment is a stent placed in the bile duct, and includes a tubular main body 11 and flaps 50 attached to both ends of the main body 11. The body has a distal end 12 and a proximal end 13 and extends along the longitudinal axis X1. The distal end 12 is an end that is placed on the liver side when placed in the bile duct. The proximal end 13 is an end that is placed on the duodenal papilla side when placed in the bile duct.

Figure 3:
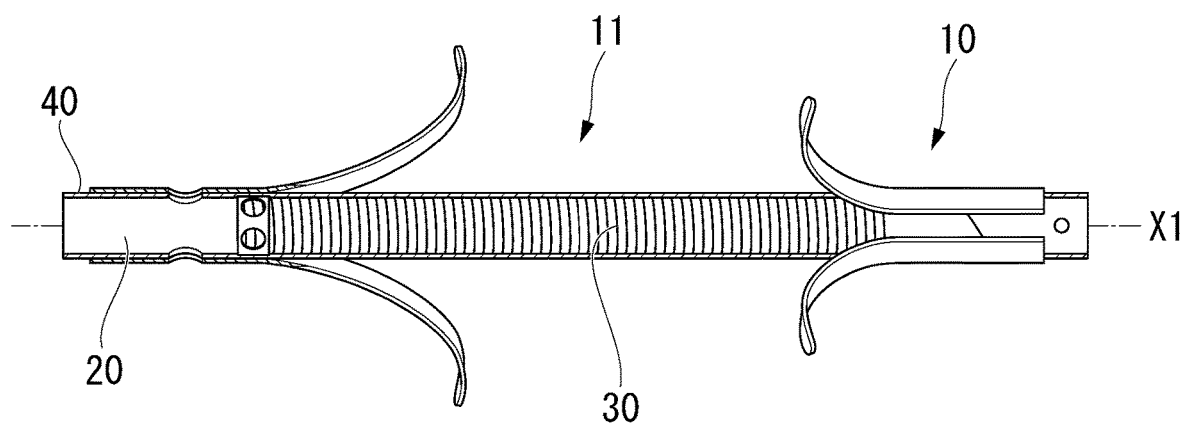
FIG. 3 is a diagram showing an internal structure of the stent.

FIG. 3 is a diagram showing the internal structure of the stent 10. The main body 11 has a resin inner layer 20, a metal wire rod 30 wound around the inner layer 20, and a resin outer layer 40 covering the inner layer 20 and the wire rod 30. The wire rod is embedded between the inner peripheral surface and the outer peripheral surface of the main body 11.

The inner layer 20 is a tube formed of a resin material having a smooth surface and biocompatibility, such as PTFE (polytetrafluoroethylene) and PFA (perfluoroalkoxy alkane).

The wire rod 30 is wound in a spiral shape on the outer peripheral surface of the inner layer 20, and is formed in a coil shape as a whole. The material of the wire rod 30 is a material having X-ray impermeableness such as tungsten steel and stainless steel.

The outer layer 40 is made of a resin material having elasticity, flexibility and biocompatibility such as urethane or polyethylene. The outer layer 40 is also provided in a gap between adjacent wire rods 30 in the longitudinal axis X1 direction.

Figure 4:
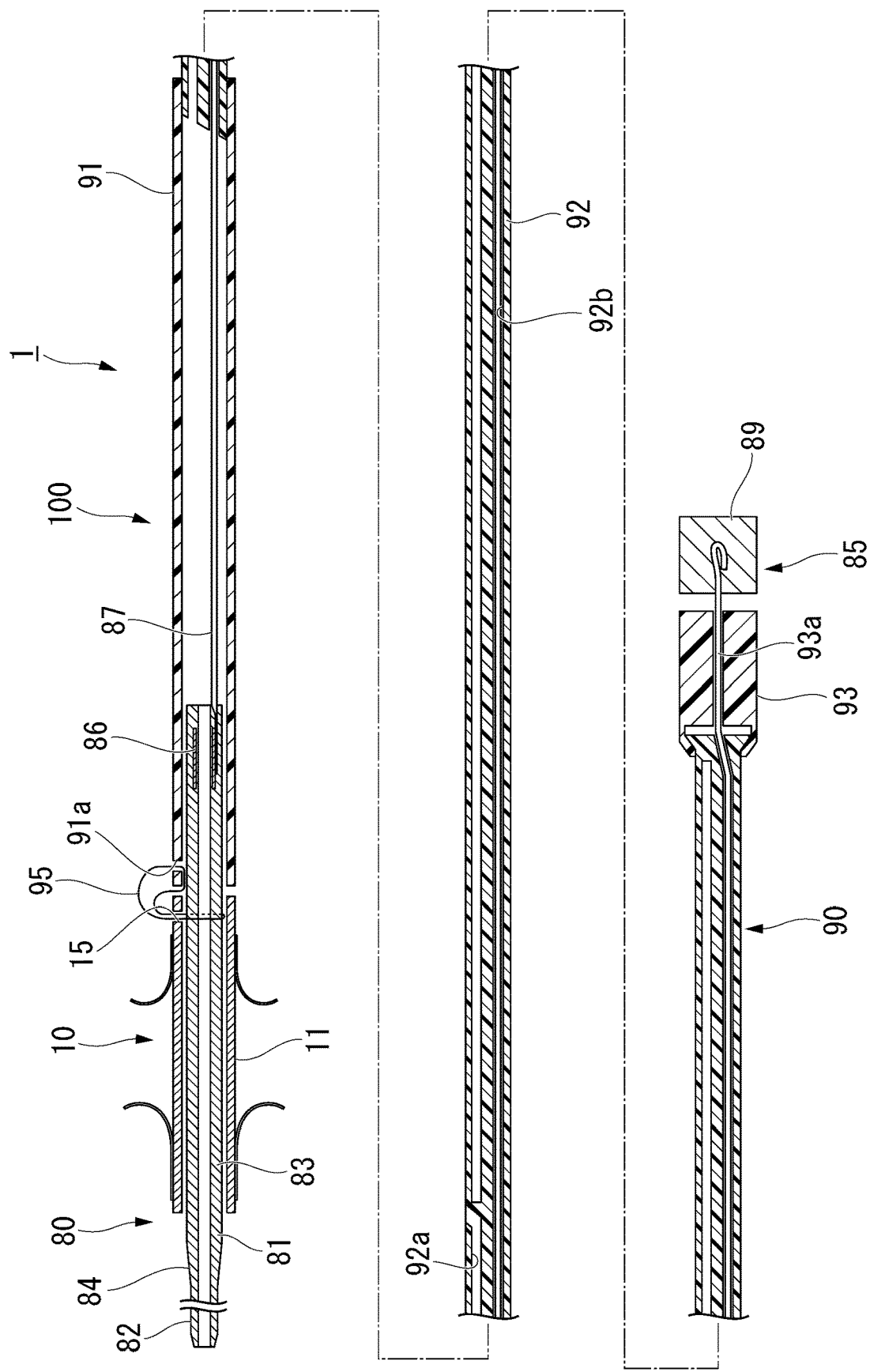
FIG. 4 is a schematic cross-sectional view of the stent delivery device.

FIG. 4 is a schematic cross-sectional view showing the structure of the stent delivery device 1. The delivery catheter 100 includes a guide catheter 80 and a pusher catheter 90.

The guide catheter 80 has a tube (guide tube) 81 through which a guide wire can be inserted, and a traction portion 85 for moving the tube 81.

The tube 81 is a tubular member made of resin and has a cavity through which a guide wire can be inserted. The tube 81 is flexible enough to be deformed when the tube 81 comes into contact with a living tissue when the stent delivery device 1 is used. The tube 81 is an elastic member having a restoring force, and becomes linear due to the restoring force in a state where no external force is applied. The tube 81 has a small diameter portion (guide tube distal end portion) 82 located on the distal end side of the delivery device 1 and a large diameter portion 83 located on the proximal end side of the delivery device 1. The boundary between the outer peripheral surface of the small diameter portion 82 and the large diameter portion 83 is a tapered intermediate portion 84, and the small diameter portion 82 and the large diameter portion 83 are connected without a step. As a result, the outer diameter of the tube 81 gradually increases from the small diameter portion 82 toward the large diameter portion 83.

The outer diameters of the small diameter portion 82 and the large diameter portion 83 are smaller than the inner diameter of the stent 10. Therefore, the tube 81 can be inserted into the stent 10.

The material of the tube 81 is made of a fluororesin, a thermoplastic resin, or the like, and the following can be exemplified. The material is not particularly limited as long as the desired mechanical properties of the tube 81 are satisfied.

Olefin resins such as polypropylene and polyethylene, their copolymer resins, polyester resins such as polyethylene terephthalate (PET) and polybutylene terephthalate (PBT), and general-purpose resins such as polyvinyl alcohol (PVA).

Engineering resins such as polyamide-based resins, fluorine-based resins (for example, polytetrafluoroethylene (PTFE), polyvinylidene fluoride (PVDF), PFA, FEP, ETFE, etc.), polyetheretherketone (PEEK), and the like.

In addition, various elastomer resins (polystyrene-based, polyolefin-based, polyurethane-based, polyester-based, polyamide-based, polyvinyl chloride-based, etc.), silicone-containing resins, polyurethane-based resins, etc.

The traction portion 85 includes a pipe (joint portion) 86, a wire (operating wire) 87, and an operating portion 89. The pipe 86 is a metal tubular member having both ends open in the axial direction. The pipe 86 is mounted in the tube 81 coaxially with the tube 81. The pipe 86 is arranged at the proximal end portion of the large diameter portion 83.

Examples of the material of the pipe 86 include a metal such as stainless steel and an engineering resin such as PEEK, but other materials may be used as long as the desired mechanical properties are satisfied.

The distal end of the wire 87 is joined to the pipe 86, and the proximal end is connected to the operating portion 89.

As the material of the wire 87, the same material as that of the pipe 86 can be exemplified. Other materials may be used as long as they satisfy the desired mechanical properties.

Figure 5:
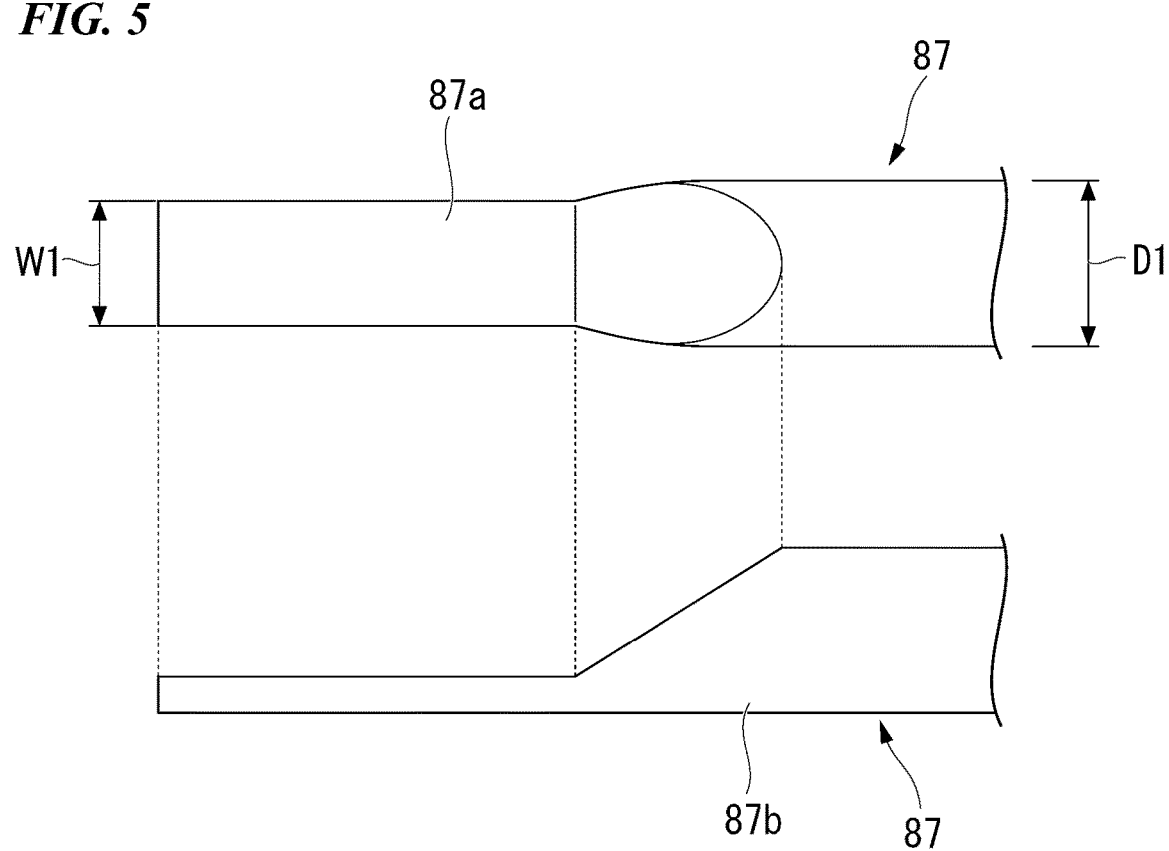
FIG. 5 is a diagram showing a distal end of a wire.

A distal end portion 87a of the wire 87 is flattened as shown in FIG. 5. The width w1 of the distal end portion 87a is smaller than the diameter D1 of the wire 87.

Figure 6:
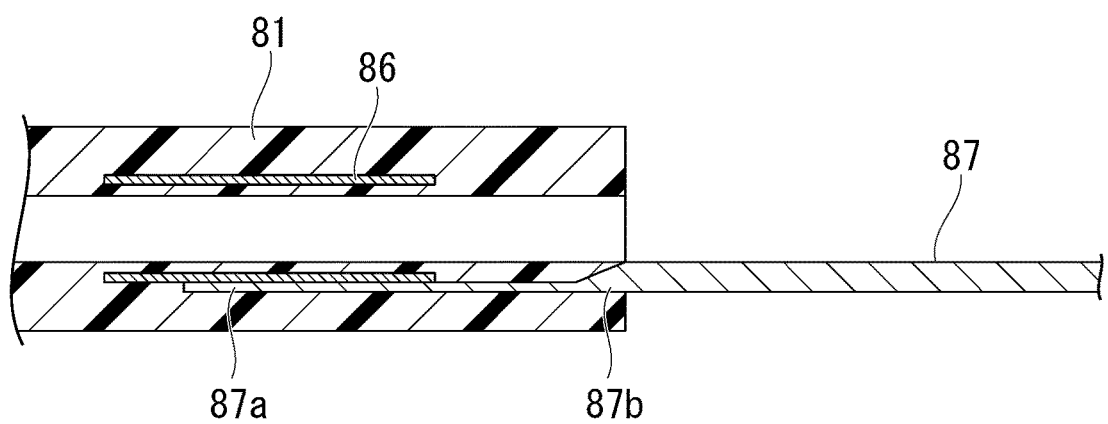
FIG. 6 is a cross-sectional view showing a joint portion between a tube and a wire.

FIG. 6 is a diagram showing a proximal end portion of the tube 81. The pipe 86 and the wire 87 are connected by joining the distal end portion 87a to the outer peripheral surface of the pipe 86. Since the width w1 of the distal end portion 87a is smaller than the diameter D1 of the wire 87, the joint area between the pipe 86 and the wire 87 does not become excessively large, and a sudden change in rigidity at the joint portion is suppressed. Of the wires 87, a boundary portion 87b at which the maximum radial dimension begins to decrease is buried in the wall of the tube 81.

The pusher catheter 90 has a single lumen tube (second tube) 91, a multi-lumen tube (first tube) 92, and a grip portion 93.

The single lumen tube 91 is a tubular member having an inner diameter into which the large diameter portion 83 of the tube 81 can be inserted. The single lumen tube 91 has flexibility. The distal end surface of the single lumen tube 91 is a plane orthogonal to the center line of the single lumen tube 91. The distal end surface of the single lumen tube 91 contacts the proximal end of the stent 10 to support the stent 10. The size of the wall thickness of the single lumen tube 91 is equal to or larger than the difference between the inner radius and the outer radius of the main body 11 of the stent (that is, the wall thickness of the stent 10). The single lumen tube 91 has a length that allows the large diameter portion 83 of the tube 81 to be completely accommodated inside the single lumen tube 91.

The multi-lumen tube 92 is fixed to the proximal end of the single lumen tube 91. The multi-lumen tube 92 has a communication passage 92a for inserting a guide wire and a wire lumen (first lumen) 92b. The wire 87 of the guide catheter 80 is inserted through the wire lumen 92b.

The communication passage 92a is open to the distal end of the multi-lumen tube 92 and is open to the side surface of the multi-lumen tube 92 on the proximal end side of the distal end of the multi-lumen tube 92.

The wire lumen 92b is open at the distal end and proximal end of the multi-lumen tube 92.

The grip portion 93 is connected to the proximal end portion of the multi-lumen tube 92. The grip portion 93 has a substantially cylindrical shape having a diameter larger than that of the multi-lumen tube 22. The outer peripheral surface of the grip portion 93 may be formed with irregularities or the like to prevent slipping.

The grip portion 93 is formed with a through hole 93a that communicates with the wire lumen 92b. The through hole 93a is located on an extension line toward the proximal end side of the center line of the multi-lumen tube 92. The through hole 93a does not have to be on an extension of the center line of the multi-lumen tube 92.

The wire 87 of the guide catheter 80 is inserted through the through hole 93a. As a result, the wire 87 and the operating portion 89 extend from the through hole 93a.

As the single lumen tube 91 and the multi-lumen tube 92, those having the same type of material to be blended but different only in the blending ratio can be preferably used. In this case, when both are welded and joined, it is easy to adjust the desired bending rigidity while maintaining the joining strength.

As the resin material of the single lumen tube 91 and the multi-lumen tube 92, the same resin as the tube 81 can be used. For example, when a relatively soft elastomer resin and a relatively hard thermoplastic resin are blended and the blending ratio of the thermoplastic resin in the multi-lumen tube 92 is higher than that of the single lumen tube 91, the flexural rigidity of the single lumen tube 91 can be made smaller than the flexural rigidity of the multi-lumen tube 92 to improve the insertability of the delivery catheter 100.

The following is an example of the configuration of the pusher catheter 90 including the single lumen tube 91 and the multi-lumen tube 92, but the configuration of the present embodiment is not limited to this example.

Multi-lumen tube 92: A tube-molded compound material containing polypropylene (Rockwell hardness (R-scale): 80), styrene elastomer (durometer A hardness: 90), barium sulfate (particle size distribution 1-100 µm: 1 µm to 10 µm cumulative frequency 80%) in a predetermined ratio.

Single lumen tube 91: A tube-molded compound material containing the above polypropylene, styrene-based elastomer, and barium sulfate in a predetermined ratio.

A pusher catheter is obtained by welding the two by heating.

A hole 91a communicating with the internal space is provided at the distal end of the single lumen tube 91. A thread (connecting member) 95 is passed through the hole 91a. The end of the thread 95 is tied to form a loop. The looped thread 95 enters the main body 11 of the stent 10 through the through hole 15 provided at the proximal end portion of the stent 10. The tube 81 of the guide catheter 80 passes through the loop of the thread 95 within the stent 10. When the operating portion 89 is pushed in to advance the guide catheter 80 to the maximum extent, the intermediate portion 84 of the tube 81 is exposed from the stent 10 held by the thread 95 on the pusher catheter 90.

As the material of the thread 95, for example, nylon can be exemplified.

Dimensional examples of each part of the delivery catheter 100 are shown below, but the configuration of this embodiment is not limited to this example.

Overall length of guide catheter 80: 2100 mm to 2300 mm
Length of tube 81: 350 mm to 450 mm
Length of wire 87: 1750 mm to 1850 mm
Overall length of pusher catheter 90: 1700 mm to 1800 mm
Overall length of single lumen tube 91: 480 mm to 520 mm
Overall length of multi-lumen tube 92: 1220 mm to 1280 mm The operation when the stent delivery device 1 configured as described above is used will be described.

The operator passes the guide wire through the channel of the side-viewing endoscope and inserts the guide wire into the bile duct while observing with the endoscope. Subsequently, the operator operates the guide wire under fluoroscopy to breach the stenosis site in the bile duct and move the distal end of the guide wire closer to the liver than the stenosis site.

The operator inserts the proximal end of the guide wire protruding from the forceps opening of the endoscope into the distal end opening of the tube 81 of the stent delivery device 1 to which the stent 10 is mounted. The guide wire enters the lumen of the single lumen tube 91 through the proximal opening of the tube 81. Further, the operator causes the proximal end portion of the guide wire to enter the guide wire lumen 92a and protrude from the proximal end side opening of the guide wire lumen 92a.

The operator inserts the stent delivery device 1 through which the guide wire is passed into the channel of the endoscope, and projects the distal end of the stent delivery device 1 from the distal end of the channel. The operator operates the riser of the endoscope to direct the distal end of the stent delivery device 1 toward the duodenal papilla and allow the stent delivery device 1 to enter the bile duct along the guide wire. In a state where the stent 10 is positioned on the pusher catheter 90 by the thread 95, the distal end of the large diameter portion 83 of the tube 81 projects from the distal end of the stent 10. As shown in FIG. 4, since the difference between the outer diameter of the large diameter portion 83 and the inner diameter of the stent 10 is small, there is no large gap between the stent 10 and the tube 81, and the operation for breaching the stenosis site is easy.

When the distal end of the stent 10 breaches the stenosis site St and the flap 50 on the distal end side moves to the liver side of the stenosis site St, the operator advances and retracts the stent delivery device 1 to determine the placement position of the stent 10. In the stent delivery device 1, as long as the tube 81 passes through the loop of the thread 95, the stent 10 does not come off the pusher catheter 90. Therefore, the stent 10 can be pulled back by retracting the stent delivery device 1. As such, the position of the stent 10 can be easily adjusted.

After determining the placement position of the stent 10, the operator pulls the operating portion 89 toward the hand while holding the pusher catheter 90. Then, the wire 87 and the tube 81 retract, but the stent 10 does not retract because it is in contact with the pusher catheter 90. When the tube 81 retracts and comes out of the stent 10 and the thread 95, the thread 95 disengages the stent 10 from the pusher catheter 90 and places the stent 10 in a desired position within the bile duct.

Figure 7:
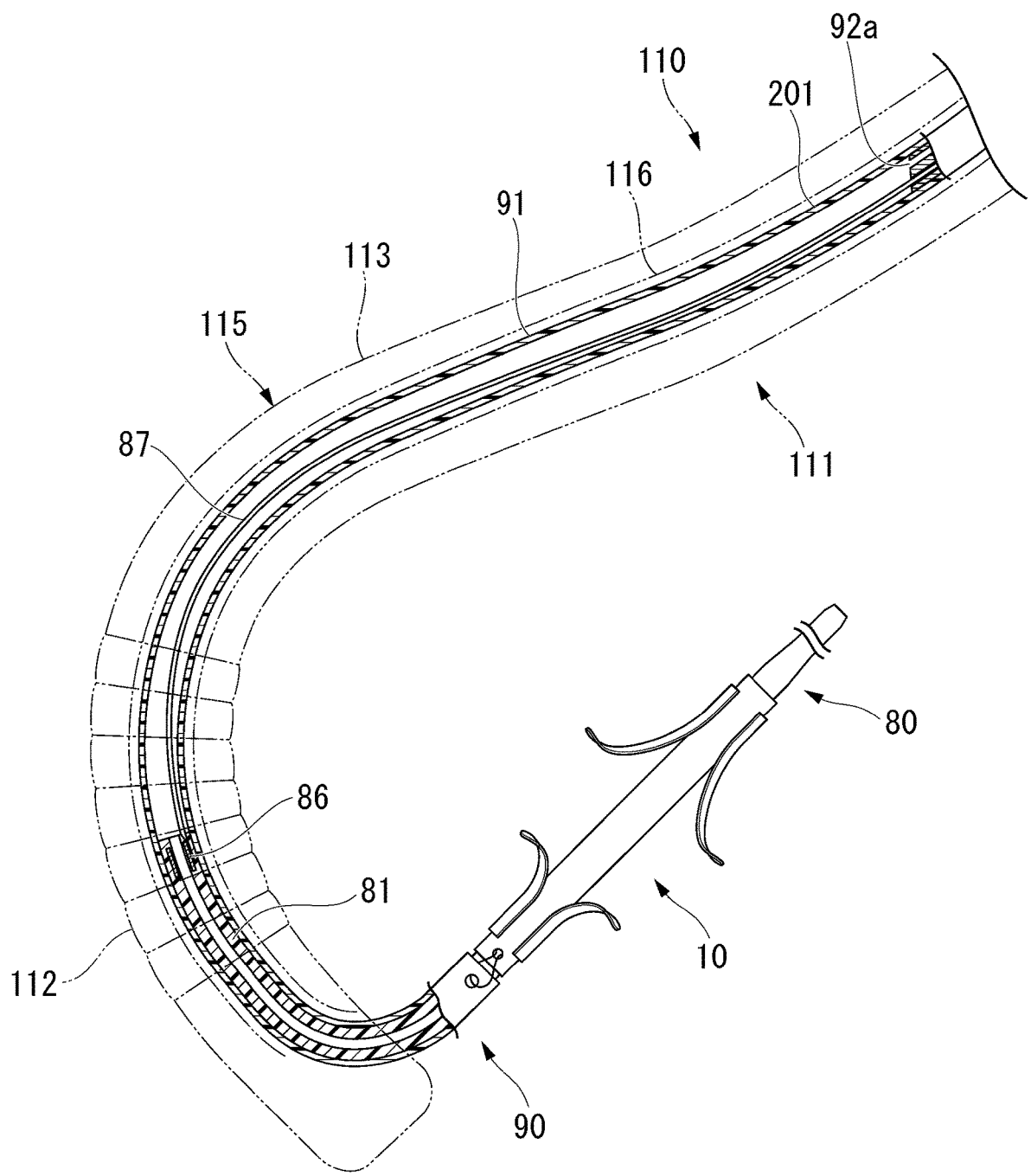
FIG. 7 is a diagram showing a positional relationship between an endoscope and a conventional stent delivery device when a stent is placed.
Figure 8:
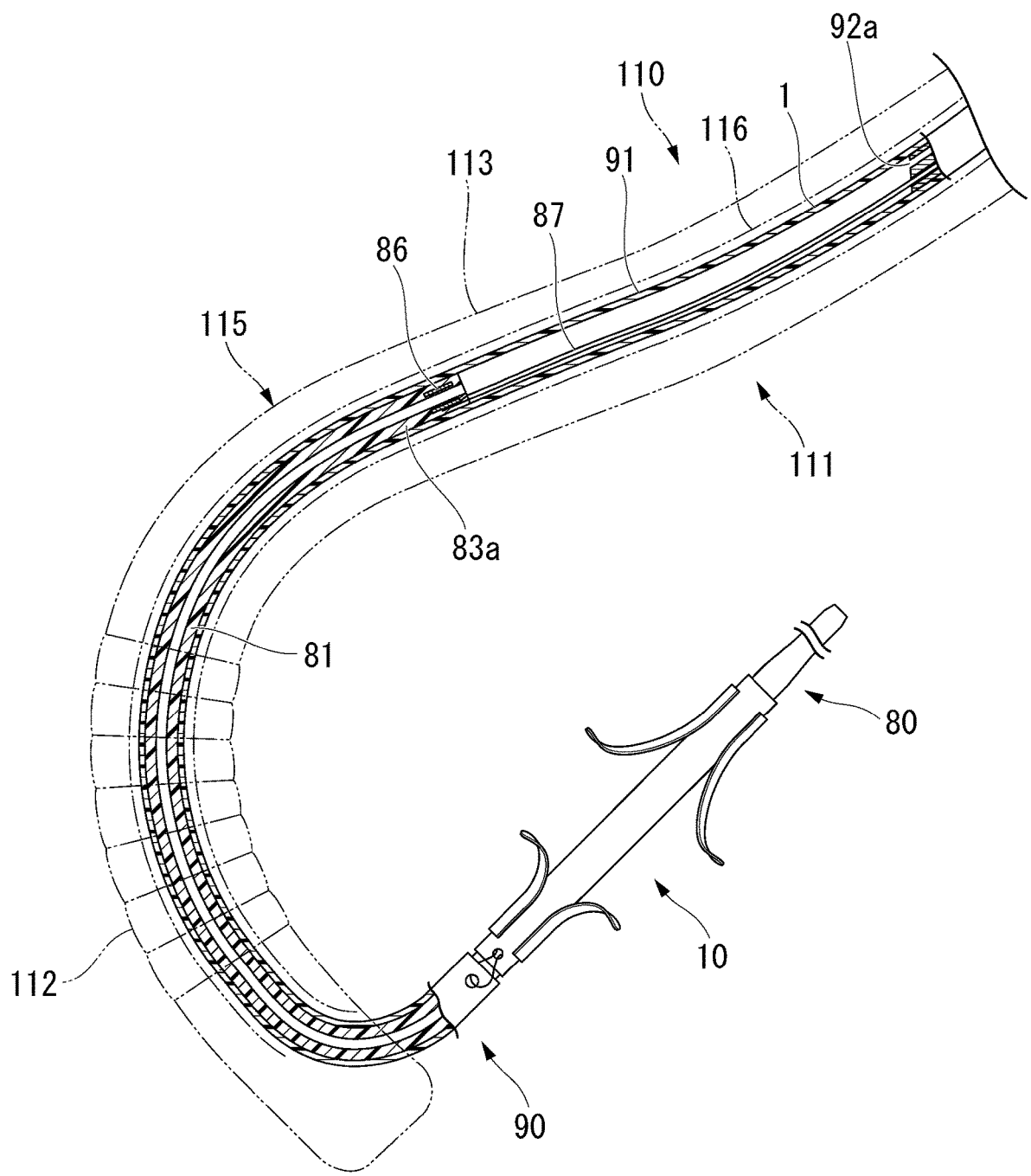
FIG. 8 is a diagram showing an example of a positional relationship between an endoscope and a stent delivery device when a stent is placed according to an embodiment of the present disclosure.

FIGS. 7 and 8 show the shape of the delivery catheter when retracting the wire 87 and tube 81. The distal end of the endoscope 110 protruding from the pylorus gently curves along the duodenum and extends to the vicinity of the duodenal papilla. As a result, of the insertion portion 111 of the endoscope 110, the curved portion 112 whose angle can be operated and a part of the flexible tube portion 113 connected to the proximal end side thereof become the curved region 115. Therefore, also in the stent delivery device 1 passed through the channel 116 of the endoscope 110, the portion located in the curved region 115 is curved according to the shape of the curved region 115.

In order to release the stent 10, it is necessary to secure an area where the guide catheter 80 can retract. Therefore, the single lumen tube 91 is always located in the curved region 115. The tube 81 and the wire 87 pass through the lumen (second lumen) of the single lumen tube 91, and the proximal end portion of the tube 81 is located at a position away from the communication passage 92a.

In the conventional stent delivery device 201, as shown in FIG. 7, in a state where the distal ends of the stent 10 and the pusher catheter 90 protrude from the channel 116 of the endoscope 110, the proximal end of the tube 81 including the pipe 86 is located in the curved portion 112 and the wire 87 is located in the curved region 115. In this case, when the operator pulls the operating portion toward the hand side, the wire 87 tries to move to the outside of the curve in the curve region 115 by its own elastic force. Since the wire 87 is thinner and harder than the tube 81, the wire 87 is pressed against the inner wall of the single lumen tube 91 with a large force in the curved region 115. Since the bending rigidity of the wire 87 is higher than the bending rigidity of the single lumen tube 91, a large frictional force is generated between the single lumen tube 91 and the wire 87, or the wire bites into the inner wall of the single lumen tube 91. Thereby, the amount of force required to pull the operating portion may become large, or it may become difficult to pull the operating portion.

The stent delivery device 1 of the present embodiment is configured based on the above. That is, in a state where the stent delivery device 1 is inserted into the endoscope 110 and the stent 10 is projected from the endoscope 110, as shown in FIG. 8, the proximal end portion of the tube 81 including the pipe 86 is located closer to the proximal end of the endoscope 110 than the curved region 115, that is, proximal to the proximal end of the curved portion 112. Therefore, when the operator pulls the operating portion 89 toward the hand to release the stent 10, the tube 81 is located within the curved region 115. Since the tube 81 has a larger diameter than the wire 87 and is softer than the wire 87, a large frictional force is not generated between the single lumen tube 91 and the tube 81, and the tube 81 does not bite into the inner wall of the single lumen tube 91.

Figure 9:
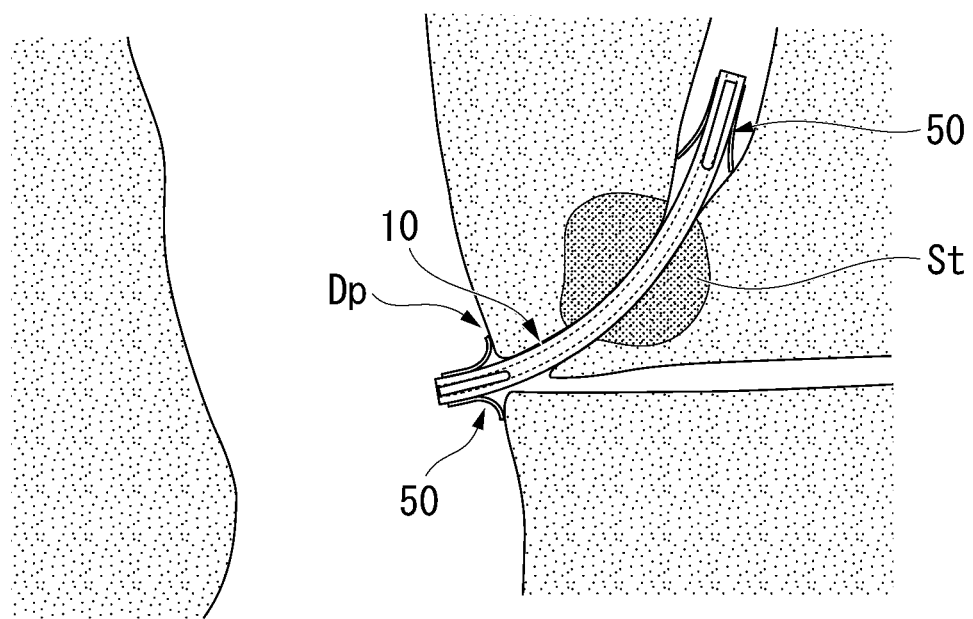
FIG. 9 is a diagram showing an indwelling stent.

After placement of the stent 10, as shown in FIG. 9, the flap 50 is placed closer to the liver side than the stenosis site St and near the duodenal papilla Dp outside the bile duct, so that the placement position is preferably maintained.

As described above, in the stent delivery device 1 of the present embodiment, a part 83a of the large diameter portion 83 on the proximal end side of the tube 81 functions as a bite prevention portion, to prevent the guide catheter 80 from biting into the pusher catheter 90. As a result, it is possible to prevent the operation of placing the stent 10 from becoming heavy or difficult, and the stent 10 can be easily released from the delivery catheter 100.

Further, since it is not necessary to thicken the wall surface of the single lumen tube 91 in order to prevent the guide catheter 80 from biting into the guide catheter 80, the large diameter portion 83 of the tube 81 can be made thicker and the inner diameter of the stent 10 can be made larger. As a result, it can be expected that the patency period after placement of the stent 10 will be lengthened and the frequency of replacement will be reduced.

Further, as compared with a method in which the surface of the wire 87 is coated to make it slippery, it can be carried out at low cost and has the same biting effect, so that it is excellent in terms of cost effectiveness.

Although each embodiment of the present disclosure has been described above, the technical scope is not limited to the above-described embodiments, and it is possible to change the combination of components, make various changes to each component, and omit them without departing from the spirit of the present disclosure.

Some changes are shown below, but not all, and other changes are possible.

In the present disclosure, the configuration of the bite prevention portion is not limited to the above-described contents.

Figure 10:
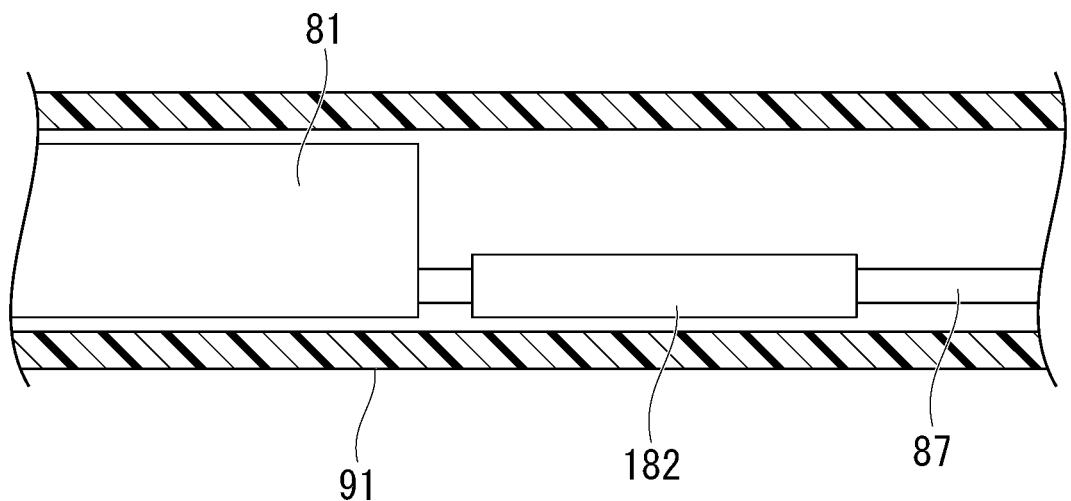
FIG. 10 is a partially enlarged view of a stent delivery device according to an embodiment of the present disclosure.

In the modified example shown in FIG. 10, the wire 87 is passed through a bite prevention tube 182 different from the tube 81. Even in this way, the guide catheter 80 can be prevented from biting into the pusher catheter 90 by locating the bite prevention tube 182 in the curved region 115 while the stent 10 is projected from the endoscope 110.

Figure 11:
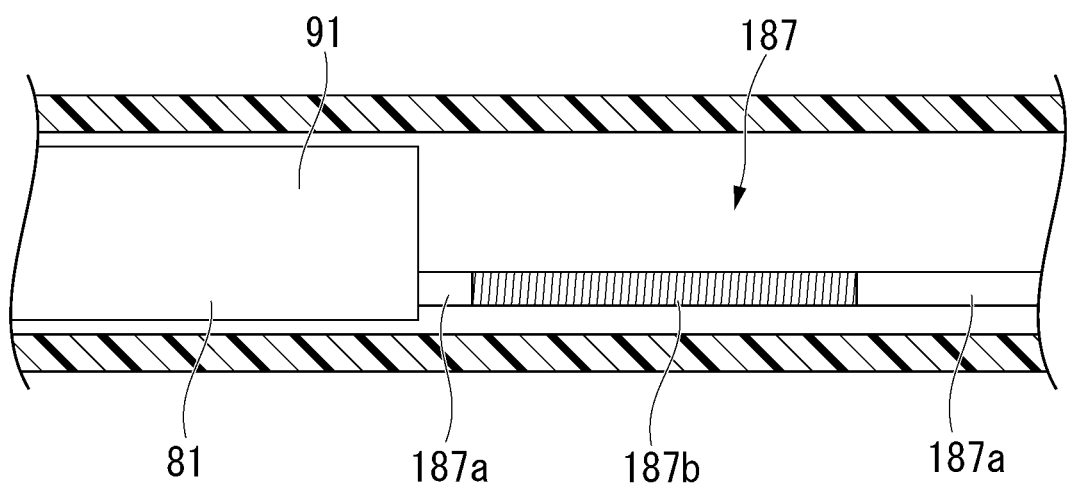
FIG. 11 is a partially enlarged view of a stent delivery device according to an embodiment of the present disclosure.

In the modified example shown in FIG. 11, the wire 187 is configured by connecting the single wire 187a and the stranded wire 187b. The single wire 187a and the stranded wire 187b can be connected by welding, caulking using a pipe, or the like. In the configuration of this modification, the stranded wire 187b functions as a bite prevention portion. That is, by locating the stranded wire 187b in the curved region 115 in a state where the stent 10 is projected from the endoscope 110, it is possible to prevent the guide catheter 80 from biting into the pusher catheter 90.

The stent in the present disclosure is not limited to that having the above-described structure. That is, the stent in the present disclosure may be a so-called pigtail type stent in which at least one end is rolled in a loop shape when the tube 81 is pulled out, and it is not essential to include the flap 50.

The present disclosure can be applied to a stent delivery device.

What is claimed is:

1. A stent delivery device comprising:
   a guide catheter including:
      a guide tube configured to receive a guide wire through an opening therein, and configured to receive a tubular stent on an outer surface thereof,
      an operating wire, and
      a joint portion mounted in a wall of the guide tube, wherein a distal end of the operating wire is fixed to a proximal end of the guide tube by the joint portion; and
   a pusher catheter including:
      a first tube having a first lumen, and
      a second tube having a second lumen, the second lumen being connected to the first lumen,
   wherein in a state where a distal end of the pusher catheter protrudes from a channel of an endoscope, the proximal end of the guide tube is configured to be positioned proximally relative to a proximal end of a bendable portion of the endoscope that is in a curved state.

2. The stent delivery device according to claim 1, further comprising a thread including a loop and being connected to the distal end of the pusher catheter,
   wherein:
      the loop is configured to be inserted into a through hole at a proximal end of the stent so as to hold the stent with respect to the pusher catheter in a state in which the guide tube is inserted into the loop, and
      in a state where the stent is held with respect to the pusher catheter and a part of the guide tube is exposed from a distal end of the stent, the joint portion is configured to be positioned proximally relative to the proximal end of the bendable portion of the endoscope that is in the curved state.

3. The stent delivery device according to claim 1, wherein a flexural rigidity of the second tube is smaller than a flexural rigidity of the operating wire.

4. The stent delivery device according to claim 1, wherein:
      the joint portion is a metal pipe,
      the guide tube has a small diameter portion and a large diameter portion having an outer diameter larger than an outer diameter of the small diameter portion, the small diameter portion being disposed distally relative to the large diameter portion,
      the distal end of the operating wire is joined to the pipe, and
      the pipe is attached to the large diameter portion so as to be coaxial with the guide tube.

5. The stent delivery device according to claim 1, wherein a width of the distal end of the operating wire is smaller than a diameter of the operating wire.

6. The stent delivery device according to claim 1, wherein a boundary portion of the operating wire at which a maximum radial dimension of the operating wire decreases distally toward the distal end of the operating wire is embedded in a wall of the guide tube.

7. The stent delivery device according to claim 1, wherein a wall thickness of the second tube is larger than a wall thickness of the stent.

8. The stent delivery device according to claim 4, wherein the second tube has a length that allows the large diameter portion to be entirely accommodated inside the second tube.

9. The stent delivery device according to claim 1, wherein a length of the guide tube is in a range of 350 mm to 450 mm.

10. The stent delivery device according to claim 1, wherein a length of the second tube is in a range of 480 mm to 520 mm.

11. The stent delivery device according to claim 4, wherein the distal end of the operating wire is joined to an outer peripheral surface of the pipe.

12. The stent delivery device according to claim 1, further comprising the stent, wherein the stent includes:
   an inner layer made of resin,
   a metal wire rod wound around the inner layer, and
   an outer layer made of resin covering the inner layer and the wire rod such that the wire rod is embedded between the inner layer and the outer layer.

13. The stent delivery device according to claim 1, further comprising a bite prevention portion configured to prevent the operating wire from biting into an inner surface of the second tube, the bite prevention portion including at least one of the following:
   a tube surrounding the operating wire,
   a stranded wire portion of the operating wire, and
   a proximal portion of the guide tube that has a larger diameter than a distal portion of the guide tube.

14. The stent delivery device according to claim 1, wherein in a state where the stent is positioned on the guide tube, the guide tube is configured to extend from within the stent into the second lumen, and the proximal end of the guide tube is positioned proximally relative to the proximal end of the bendable portion of the endoscope that is in the curved state.

15. The stent delivery device according to claim 1, wherein the first tube extends proximally relative to the second tube.

16. The stent delivery device according to claim 1, wherein the proximal end of the guide tube is positioned between the proximal end of the bendable portion that is in the curved state and a distal end of the first tube.

17. The stent delivery device according to claim 1, wherein a proximal portion of the second tube is configured to receive a distal portion of the first tube.

18. The stent delivery device according to claim 1, wherein the first tube is fixed to a proximal end of the second tube.

19. The stent delivery device according to claim 1, wherein the operating wire is inserted through at least the first lumen, and the guide tube is inserted through the second lumen.

20. The stent delivery device according to claim 1, wherein the operating wire extends along a longitudinal axis of the pusher catheter.

* * * * *